United States Patent [19]
Wieland et al.

[11] Patent Number: 5,922,900
[45] Date of Patent: Jul. 13, 1999

[54] PROCESS FOR PRODUCING CARBOXYLIC ACID ESTERS AND CATALYSTS THEREFOR

[75] Inventors: Stefan Wieland, Offenbach; Peter Panster, Rodenbach, both of Germany

[73] Assignee: Degussa Aktiengesellschaft, Frankfurt, Germany

[21] Appl. No.: 08/922,558

[22] Filed: Sep. 3, 1997

[30] Foreign Application Priority Data

Sep. 4, 1996 [DE] Germany ............................ 196 35 769

[51] Int. Cl.$^6$ .......................... C07G 67/08; C07G 67/00; C08G 79/00; C08G 77/00
[52] U.S. Cl. .............................. 560/99; 560/204; 560/98; 528/9; 528/10
[58] Field of Search .................................. 556/9, 10, 173, 556/428; 528/9, 10; 560/99, 204

[56] References Cited

U.S. PATENT DOCUMENTS

| | | | |
|---|---|---|---|
| 4,552,700 | 11/1985 | Panster ......................................... | 556/9 |
| 4,647,644 | 3/1987 | Panster et al. ............................. | 528/30 |
| 5,354,831 | 10/1994 | Panster et al. .............................. | 528/9 |
| 5,502,240 | 3/1996 | Pugach et al. ............................. | 560/90 |

OTHER PUBLICATIONS

Patent Abstracts of Japan, vol. 13, No. 549, Dec. 7, 1989.

*Primary Examiner*—Gary Geist
*Assistant Examiner*—J. Parsa
*Attorney, Agent, or Firm*—Smith, Gambrell & Russell, LLP; Beveridge, DeGrandi, Weilacher & Young

[57] ABSTRACT

A process for producing carboxylic acid esters by the following steps:

a) preparation of a reaction mixture containing an alcohol and a carboxylic acid and/or a carboxylic anhydride and/or a carboxylic acid ester and or a partially esterified carboxylic acid, b) heating of this mixture to the suitable reaction temperature in the presence of a solid polysiloxane insoluble in the reaction medium and having sulphonic acid groups with intensive thorough mixing accompanied by continuous separation of the reaction water which forms, wherein the polysiloxane used as the catalyst in modified by treatment with a soluble aluminum, titanium or zirconium compound, and the spherical particles thereof have a diameter of 0.01 to 3 mm, a specific surface of 0.1 to 1200 $m^2/g$, a specific pore volume of 0.01 to 6.0 ml/g and a bulk density of 50 to 1000 g/l.

26 Claims, 2 Drawing Sheets

- reaction temperature profile; 2h 180°C, then 150°C
- reaction temperature constant at 155°C

PROCESS FOR PRODUCING CARBOXYLIC ACID ESTERS AND CATALYSTS THEREFOR

INTRODUCTION AND BACKGROUND

The present invention relates to a process for producing carboxylic acid esters and to the catalysts suitable for catalyzing the esterification reaction. Acid-catalyzed esterifications and interesterifications are carried out as is known in the prior art, for example, with sulphuric acid or with hydrochloric acid as well as with soluble organic acids. Homogeneous acid catalysts are distinguished by particularly good activity. A disadvantage of the use of these prior methods and catalysts, however, resides in the poor separability of the desired product of esterification from the reaction product and, in particular, the need for an optionally distillative purification of the esterification product. This can cause undesirable discolorations of the product and/or product loss, particularly when higher-molecular reaction products are involved. It is also known to undertake ester formation in the presence of solid acid catalysts.

Such processes are described in EP-B-0192035 for cation exchange resins and in U.S. Pat. No. 5,502,240 for titanium containing zeolites as catalysts. According to this prior patent, phthalic esters are produced at temperatures of 210 to 230° C.

It is therefore an object of the present invention to overcome disadvantages and drawbacks of prior known methods and to provide an improved process for producing carboxylic acid esters.

It is a further object of the invention to provide new catalysts which enable the catalytic reaction of carboxylic acids to form esters.

SUMMARY OF THE INVENTION

In achieving the above and other objects, one feature of the present invention is to produce carboxylic acid esters by the following process: follows:

a) preparing a reaction mixture comprising an alcohol and a carboxylic acid and/or a carboxylic anhydride and/or a carboxylic acid ester and or a partially esterified carboxylic acid, b) heating this reaction mixture to a sufficient reaction temperature in the presence of a solid polysiloxane which is insoluble in the reaction medium and having sulphonic acid groups present, with intensive thorough mixing accompanied by continuously separating the water of reaction which forms in the course of the reaction of esterification and c) isolating the desired ester after conversion, e.g. by distillation after separation of the catalyst.

Another feature of the invention resides in novel catalysts based on organopolysiloxanes that have been modified with aluminum, titanium or zirconium compounds that are particularly well suited as catalysts for esterification reactions of the type described herein.

BRIEF DESCRIPTION OF DRAWINGS

The present invention will be further understood with reference to the accompanying drawings, wherein.

DETAILED DESCRIPTION OF THE INVENTION

Figure 1:
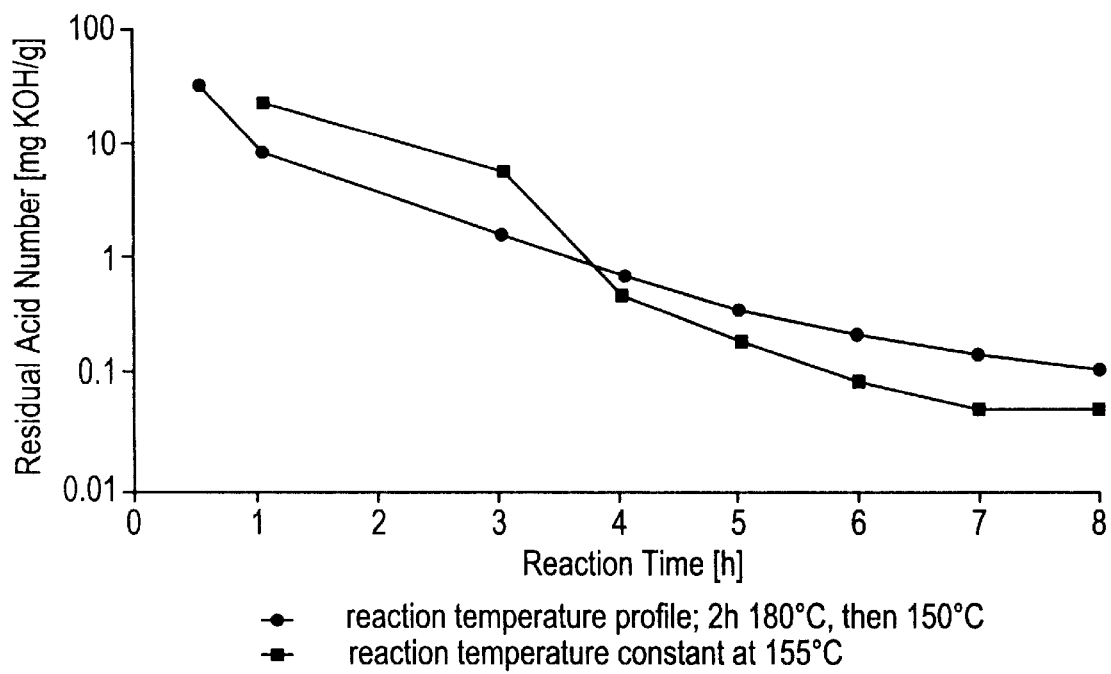
FIG. 1 is a plot of various probes of residual acid number versus reaction time.

According to the present invention, the catalysts that can be used for the esterification reaction include known catalyst and novel catalysts. The known catalyst are those described in patent specifications DE 3226093 (EP 0098946, U.S. Pat. No. 4,552,700), DE 3518881 and DE 4223539 (U.S. Pat. No. 5,354,831) all of which are relied on for the disclosure of the catalysts and are incorporated herein by reference.

The organopolysiloxanes used as catalysts according to the present invention are characterized, for example, in that they contain identical or different units of the general formula:

$$(O_{3/2}Si-R^1-SO_3^-)_xM^{x+} \quad (1)$$

in which $R^1$ is a linear or branched alkylene group with 1 to 12 C atoms, a cycloalkylene group with 5 to 8 C atoms or a unit of the formula:

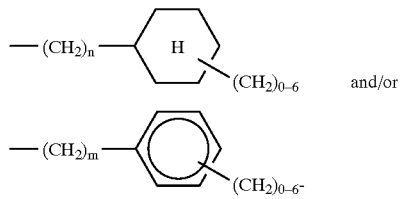

in which n may be a real integer from 1 to 6 and indicates the number of recurring methylene groups attached to sulfur, x is a real integer from 1 to 4 dependent on the valence of M, and M is hydrogen or a mono-to tetravalent metal ion, and the free valencies of the oxygen atoms are saturated with silicon atoms of at least one member of the group consisting of a unit of formula (1) and crosslinking bridge members: $SiO_{4/2}$, $R'SiO_{3/2}$, $R'_2SiO_{2/2}$, $TiO_{4/2}$, $R'TiO_{3/2}$, $R'_2TiO_{2/2}$ and $AlO_{3/2}$ wherein R' is methyl or ethyl, and/or saturated by di-, tri- and tetrasulfide units of the general formula:

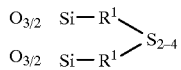

wherein $R^1$ has the same meaning as in formula (1) and may be the same or different, the ratio of the sum of the Si- atoms in formulas (1) and (2) to the bridge atoms silicon, titanium and aluminum ranging from 1:0 to 1:10.

Further particulars may be found in the patent specifications referred to above.

These prior patents also contain details of the preferably used spherical particles of this composition which have a diameter of 0.01 to 3 mm, a specific surface of 0.1 to 1200 m²/g and a bulk density of 50 to 1000 g/l. Thus, persons skilled in the art will be able to choose an appropriate known catalyst based on the foregoing disclosure to carry out the present invention.

In a preferred embodiment, catalysts of this type described above can be modified with aluminum, titanium or zirconium compounds to produce novel catalysts. These novel catalysts are obtained by treating the above-mentioned known polysiloxanes containing sulphone groups under hydrothermal reaction conditions with a solution of one or more compounds of these elements.

Generally speaking the physico/chemical parameters, such as diameter, specific surface, pore volume and bulk density for the novel catalyst of this invention are then in the above-mentioned ranges.

The soluble aluminum, titanium and/or zirconium compounds that are employed to make the novel catalyst of this invention are preferably used in the form of aqueous, alcoholic, particularly ethanolic or methanolic, solutions. These then preferably contain hydroxy complexes, acetylacetonate complexes, alkoxy compounds or other coordinate forms also.

The modification reaction to produce the novel catalysts of the invention takes place at 80 to 200° C., preferably in the temperature range from 100 to 180° C. at a pressure which corresponds to the sum of the partial pressures of the individual components.

After conversion the solid is separated off, optionally washed and then dried.

The quantity of the Al, Ti and/or Zr compounds to be used for the modification of the polysiloxanes largely depends on their concentration in the solutions used for modification.

Generally speaking this concentration is selected approximately 10% higher than that which is desired to be present on the solid polysiloxane.

It has been shown that the incorporation of Al concentrations is preferably in the range from 0.1% to 1%, that of Ti and Zr concentrations in the range from 0.1% to 5%, related to the total quantity of the solid.

These quantities are also not eliminated by washing processes.

These compounds present in oxidic form may be differentiated from the Al, Ti or Zr ions optionally originally present in the polysiloxane by analytical methods on the basis of their non-uniform distribution over the overall surface of the catalyst.

The process according to the invention is particularly suitable for producing esters of the dicarboxylic acid, phthalic acid, such as the following:
dimethyl phthalate
diethyl phthalate
dibutyl phthalate
diisobutyl phthalate
butylbenzyl phthalate
diisopentyl phthalate
diheptyl phthalate
di-2-ethylhexyl phthalate
diisooctyl phthalate
di-n-octyl phthalate
di(hexyl-octyl-decyl) phthalate
di(octyl-nonyl-decyl) phthalate
di(heptyl-nonyl) phthalate
di(heptyl-nonyl-undecyl) phthalate
di(nonyl-decyl-undecyl) phthalate
dinonyl phthalate
diisononyl phthalate
di(3,5,5-trimethylhexyl) phthalate
diisodecyl phthalate
diundecyl phthalate
diisoundecyl phthalate
diisotridecyl phthalate
di(methoxyethyl) phthalate
di(butoxyethyl) phthalate, and
preferably di-2-ethylhexyl phthalate, di-isooctyl phthalate and di-n-octyl phthalate. In this case phthalic anhydride and the corresponding alcohol are particularly used.

The phthalates are produced at temperatures of 100 to 220° C., preferably in the range from 130 to 170° C. In addition to the production of phthalates the process is also suitable, using the catalysts described above, for the esterification of free fatty acids, e.g. to form the methyl esters or to form esters with higher-molecular alcohol content (such as the esterification of fatty acids with fatty alcohols). Other polycarboxylic acids as well as monocarboxylic acids, all referred to herein as carboxylic acids can be esterified by following procedures herein based on the knowledge of persons skilled in the art.

The process according to the invention is also very important for the interesterification of fatty acid esters and particularly for the interesterification of triglycerides to the fatty acid methyl esters. The alcohol to be converted (in the case of monohydric alcohols) is preferably present at least in a molar ratio of 1:1 to 1:1.5 related to the acid groups to be esterified. Above all, the alcohols used are those with a chain length of $C_1$ to $C_{20}$, particularly $C_4$ to $C_{12}$, straight-chain or branched. With corresponding carbon value these also include cyclic alcohols with a saturated or unsaturated ring. Polyhydric alcohols are also contemplated herein.

Fatty acids may be saturated or unsaturated and contain 4 to 22 carbon atoms, usually even numbered and contain a terminal —COOH group. They are derived from animal or vegetable fat or oil; see Hawley's Condensed Chemical Dictionary, 11th Edition 1987.

The advantages of the process according to the invention chiefly lie in the fact that the reaction temperatures for carrying out the esterification reactions can be distinctly reduced compared with the prior art without the selectivity of the reaction suffering thereby.

Intensive thorough mixing of the reaction mixture in which the catalyst is present in suspended form is essential to achieving this result. This thorough mixing takes place in known manner.

At the same time it has proved important immediately to separate off the water of the reaction which forms. This takes place by distilling off the water of reaction optionally at reduced pressure or supported by an inert gas stream passed through the reaction vessel. The reaction temperature may be above or below the boiling point of the alcohol or be equal to the boiling point of the alcohol. If high-boiling alcohols are used it has, however, been shown that the process according to the invention provides particularly good results (low residual acid values, low color values) if the reaction temperature is selected to be distinctly below the boiling point of the alcohol but high enough for a reliable quantitative removal of the reaction water—assisted by an additional passage of nitrogen through the reaction vessel—to be assured.

The following examples show to illustrate the present invention.

EXAMPLE 1

Preparation of a Titanium (Ti) Containing Solid Acid Catalyst 25.69 g of $Ti(OC_3H_7)_4$ (in excess) were slowly dissolved in 300 ml of 3 N hydrochloric acid and then reacted in the presence of 380 g of a spherically shaped solid acid catalyst prepared according to DE 42 23 539 having the formula $O_{3/2}SiCH_2CH_2CH_2SO_3H \cdot 6SiO_2 \cdot 2CH_3CH_2CH_2SiO_{3/2}$ with the particle size of 0.1–0.4 mm and with a water content of 71.5 weight percent. The suspension was then converted in a Berghoff autoclave for 20 hours at 140° C. under a pressure of 21 bar. After cooling off, the product was washed several times with water and the resulting finely divided precipitated product was then separated by decantation. After that, the catalyst was washed with ethanol and then dried at 120° C. under an atmosphere of nitrogen for 12 hours.

There was obtained a titanium containing catalyst which was used in the subsequent examples for the esterification reaction.

| | |
|---|---|
| Ti content (analytically determined): | 2.26 weight % (corresponding to about 2.6 weight % titanium dioxide) |
| Yield: | 110.4 grams |
| BET-Surface Area | 450 m$^2$/g |
| Pore Volume (Total) | 3.5 ml/g |
| Particle Density | 390 g/l |

EXAMPLE 2

Stepwise Esterification of Phthalic Acid Anhydride with 2-Ethylhexanol(2-EH)

a) In a 250 ml three neck flask equipped with a KPG-stirrer, water separator and a nitrogen inlet there was introduced 44.4 g (0.30 mol) of phthalic acid anhydride and 97.58 g 2-Ethylhexanol (0.75 mol). This was then heated to 180° C. After 30 minutes there was introduced 3 grams of the catalyst produced in accordance with Example 1. This was then further stirred for 1.5 hours at a temperature of 180° C. and then vigorously stirred at 150° C. to permit further reaction. During the total reaction time the reaction mixture was subjected to a nitrogen stream over the surface in order to obtain better water separation. During this time at specific intervals, liquid probes were taken and the alcohol distilled off and the acid number of the product was determined. After 8 hours, a residual acid number of 0.14 mg KOH/g product was determined.

b) Analogous to the procedure used in a) there was an experiment conducted with a constant reaction temperature of 155° C. and the entire process was repeated. In this experiment, the catalyst was first introduced after one hour. After 8 hours of reaction time the acid number was determined to be 0.06 mg KOH/g product. The results are shown in FIG. 1.

EXAMPLE 3

Continuous Esterification of Phthalic Acid Monoester (Mono-Octylphthalate, MOP) with 2-EH.

Figure 2:
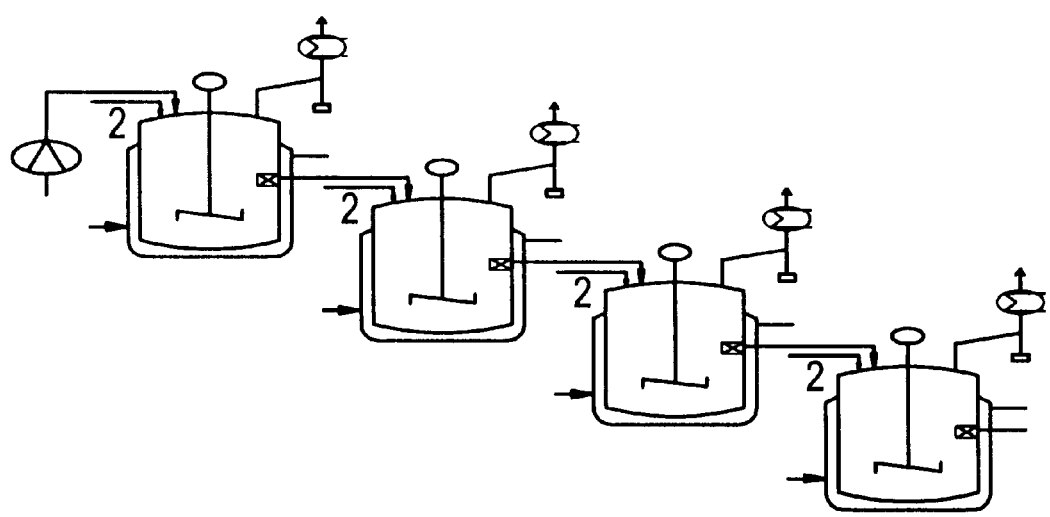
FIG. 2 is a schematic view of a reaction cascade of reactor vessels for carrying out the present invention.

Phthalic acid anhydride was dissolved in a 3 times molar amount of 2-ethylhexanol and then stirred for 5 hours at a water separator at 150° C. The so obtained partially esterified solution was then delivered to a cascade of agitation vessels with a membrane pump which is schematically illustrated in FIG. 2. The vessels are glass vessels with heated double jackets.

Each of the reaction vessels was equipped with the heated double jacket, a KPG stirrer, a water separator and a nitrogen inlet line. Into each vessel there was introduced 5 grams of a spherically formed, solid acid catalyst having the composition $O_{3/2}SiCH_2CH_2CH_2SO_3H \cdot 6SiO_2 \cdot 2CH_3CH_2CH_2SiO_{3/2}$ prepared according to the German Patent 42 23 539 with a particle size of 0.1 to 0.4 mm and with a water content of 75.3 weight %. The apparatus was then filled with 2-ethylhexanol and then under the following treatment conditions subjected to the reaction:

| Experimental Reaction Conditions: | |
|---|---|
| Feed-Rate of the Monoester (MOP): | 15 g/h |
| Filled Volume of each Glass Reaction Vessel | 75 g |
| Catalyst Introduction Per Glass Reaction Vessel | 5 g |
| Reaction Temperature | 155° C. |

After the depletion of the above amount of 2-ethylhexanol and arrival at the equilibrium point in the reaction there was obtained from the last glass vessel in the reaction cascade a colorless product and the acid number was determined to be less than 0.1 mg KOH/g. Within the time period of about 700 hours there was no change observed in the quality of the product.

EXAMPLE 4

Esterification of 3.0 Beef Tallow Fatty Acid 3 g of a catalyst having the formula: $O_{3/2}SiCH_2CH_2CH_2SO_3H \cdot 9SiO_2$ with the water content of 75 weight % was introduced into a 250 ml glass flask fitted out with a KPG stirrer, water separator and a nitrogen inlet port. To this there was added 150 g of a mixture of free beef tallow fatty acid (acid number 203 mg KOH/g) and 1-Octanol. The resulting reaction mixture was stirred at a 165° C. with a weak stream of nitrogen. After specific time intervals probes were taken and these were analyzed. The following acid numbers were therefore determined:

| Reaction Time in hours | 0 | 0.25 | 0.5 | 0.75 | 1.0 | 1.5 | 2.5 | 3.0 |
|---|---|---|---|---|---|---|---|---|
| Acid Number in [mgKOH/g] | 203 | 65 | 19 | 5 | 1.8 | 0.5 | 0.18 | 0.09 |

EXAMPLE 5

Esterification of Oleic Acid

In the cascade of stirred reaction vessels illustrated in Example 3, oleic acid and a variety of alcohols in a molar ratios of 1:3 were introduced. Thus the acid and the alcohols were directly reacted without preesterification. In each stirred reaction vessel there was introduced 3.0 g dry catalyst with the formula $O_{3/2}SiCH_2CH_2CH_2SO_3H \cdot 6SiO_2 \cdot 2CH_3CH_2CH_2SiO_{3/2}$. The parameters and the experimental reaction conditions are shown in the following table:

| Introduced Alcohol | Esterification Temperature [° C.] | Throughput [g/h] | Final Acid Number [mg/KOH/g] |
|---|---|---|---|
| n-Hexanol | 150 | 5.25 | 0.22 |
| 4-Methyl-2-pentanol | 135 | 3.81 | 1.26 |
| 2-butanol | 110 | 8.70 | 8.50 |

EXAMPLE 6

Preparation of Butylacetate a) In a 250 ml three neck flask equipped with a KPG-stirrer, a water separator and a reflux condenser there was introduced 12 g (23.8 ml) of dry catalyst of the composition $O_{3/2}SiCH_2CH_2CH_2SO_3H \cdot 9SiO_2$. After that, 90.0 g of glacial acetic acid and 122 g of n-butanol were introduced. With vigorous stirring (270 rpm) the suspension was heated in an oil bath up to 130° C. At definite time periods probes were taken and these were analyzed by a gas chromatography apparatus to determine the formed butyl acetate.

b) An identical experiment was run as in a) where however, only 6 g (11.9 ml) of the above described catalyst was used.

c) This experimental was carried out in an identical way as is described in a) except that only 3 g (5.95 ml) of the above-described catalyst was used.

Figure 3:
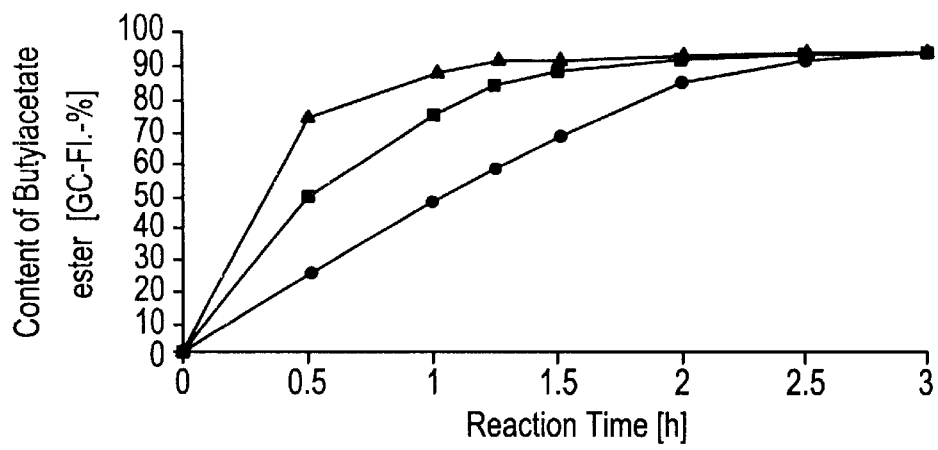
FIG. 3 is a plot of content of butylacetate ester versus reaction time according to the present invention.

FIG. 3 shows the increase in the butyl acetate concentration in the reaction solution as a result of the series of experiments. The speed of the arrival at the end point of the reaction (residue is excess n-Butanol) is dependent on the catalyst concentration (12 g corresponds to 10 Vol. %; 6 g corresponds to 5 Vol. %; 3 g corresponds to 2.5 Vol. %.). The solution after the end of the reaction has the following typical composition n-Butanol: 8.6 Fl % Butylacetate: 91.4 Fl %: Acidic Acid, Water: about less than 0.1 Fl %).

The esterification may be conveniently carried out stepwise in the form of a reaction cascade as shown in FIG. 2. Partially esterified material is thus further esterified in the reaction cascade sequences and finally converted in the last reaction cascade until the desired residual acid value is reached. The excess alcohol can be removed by distillation in the last reaction cascade vessel.

It has proved particularly favorable in order to suppress the formation of by-products from the alcohol when the reaction temperature for esterification is below the boiling point of the alcohol and the alcohol is removed by distillation only when the crude product mixture has been separated from the catalyst. The process can be advantageously carried out for example in a cascade of stirred-tank reactors or in the form of several series fixed-bed reactors with intermediate distillation stages in each case to remove the water of reaction. The effects of subsequent surface modification of the catalysts are noticed in particular in the increase in selectivity in catalytic conversions. By incorporating aluminate units by means of this subsequent modification, in the range from 0.1% to 1% the susceptibility to hydrolysis of the polysiloxane matrix under hydrothermal reaction conditions is reduced. By incorporating titanium oxide and/or zirconium oxide units the selectivity of the catalysts is improved by reducing the formation of by-products from the alcohol used (olefin formation, ether formation). The advantages of the process according to the invention and of the catalysts according to the invention are demonstrated, for example, in the esterification of phthalic anhydride with 1-octanol or 2-ethylhexanol as shown in examples 2 and 3. If the process according to the invention is implemented in this case at a reaction temperature of 150 to max. 160° C. and a titanium-modified catalyst (titanium content 5 wt. %) is used, after separation of the crude product mixture from the catalyst and distillative separation of the excess alcohol a residual acid value of the diester of <0.1 mg KOH/g is obtained, and the 2-ethylhexanol phase distilled off contains by-products such as olefins and ethers in a content by weight of <0.5 wt. %.

The esterification of free beef tallow fatty acid with 1-octanol takes place at a reaction temperature between 150 and 180° C. The reaction product obtained has a residual acid value of <0.2 mg KOH/g.

Further variations and modifications of the foregoing will be apparent to those skilled in the art and are intended to be encompassed by the claims appended hereto.

German priority application 196 35 769.1 is relied on and incorporated herein by reference.

We claim:

1. A process for producing a carboxylic acid ester, comprising:
    a) preparing a reaction mixture of an alcohol and a carboxylic acid and/or a carboxylic anhydride and/or a carboxylic acid ester and or a partially esterified carboxylic acid, to thereby obtain a reaction mixture in a reaction medium,
    b) heating said mixture to a sufficient reaction temperature in the presence of a catalyst which is a solid polysiloxane insoluble in said reaction medium and having sulphonic acid groups with intensive thorough mixing accompanied by continuously separating water of reaction which forms,
    wherein a surface of said polysiloxane is modified by 0.1% to 1% related to the total quantity of the solid of oxidic aluminum compounds or said polysiloxane is modified by 0.1% to 5% related to the total quantity of oxidic titanium or zirconium.

2. The process according to claim 1 further comprising isolating the desired ester.

3. The process according to claim 1, wherein said surface of said polysiloxane has been modified by reacting a soluble titanium, zirconium and/or aluminum compound with said polysiloxane at 80 to 200° C.

4. The process according to claim 1 wherein the reaction temperature is 100 to 220° C.

5. The process according to claim 1 further comprising passing an inert gas stream through the reaction mixture to remove the water of reaction.

6. The process according to claim 1 wherein said catalyst is used in a quantity of up to 15 wt. %, based on the weight of the reaction mixture.

7. The process according to claim 1 wherein said alcohol has a chain length of $C_1$ to $C_{20}$.

8. The process according to claim 7, wherein said alcohol has a chain length of $C_4$ to $C_{12}$.

9. The process according to claim 1 wherein a free fatty acid is the carboxylic acid.

10. The process according to claim 1 wherein a fatty acid is esterified with a fatty alcohol.

11. The process according to claim 1 wherein phthalic anhydride, phthalic acid and/or phthalic acid monoester is used as said acid.

12. The process according to claim 1 wherein the molar ratio of alcohol present in the reaction mixture and acid groups to be esterified is between 1:1 and 1:1.5.

13. The process according to claim 11 wherein isooctyl or 1-octyl alcohol is used for esterification.

14. The process according to claim 11 wherein the esterification is carried out at a temperature of 100 to 180° C.

15. The process according to claim 12 wherein the esterification is carried out at a temperature of 100 to 180° C.

16. The process according to claim 12 wherein isooctyl or 1-octyl alcohol is used for esterification.

17. The process according to claim 13 wherein the esterification is carried out at a temperature of 100 to 180° C.

18. The process according to claim 1 wherein the temperature of reaction is below the boiling point of the alcohol.

19. The process according to claim 18 wherein the alcohol is removed by distillation after the ester has been separated from the catalyst.

20. A polysiloxane comprising
    a polysiloxane containing sulphonic acid groups, wherein a surface is modified by 0.1% to 1% of oxidic aluminum compounds, related to the total quantity of the solid.

21. A polysiloxane comprising
a polysiloxane containing sulphonic acid groups, wherein a surface thereof is modified by 0.1% to 5% of oxidic titanium or zirconium compounds related to the total quantity of the solid.

22. Polysiloxane according to claim 20 wherein the spherical particles have a diameter of 0.01 to 3 mm, a specific pore volume of 0.01 to 6.0 ml/g and a bulk density of 50 to 1000 g/l.

23. Polysiloxane according to claim 21 wherein the spherical particles have a diameter of 0.01 to 3 mm, a specific pore volume of 0.01 to 6.0 ml/g and a bulk density of 50 to 1000 g/l.

24. A process for producing the surface-modified polysiloxane containing sulphonic acid groups defined in claim 20, comprising converting a solid polysiloxane in an alcoholic, neutral, alkaline or acid medium at temperatures of 80 to 200° C. with a dissolved aluminum compound to form said surface-modified polysiloxane, and separating the modified polysiloxane optionally washed and then dried.

25. A surface modified polysiloxane produced by the process of claim 24.

26. A process for producing the surface-modified polysiloxane containing sulphonic acid groups defined in claim 21, comprising converting a solid polysiloxane in an alcoholic, neutral, alkaline or acid medium at temperatures of 80 to 200° C. with a dissolved titanium or zirconium compound to form said surface-modified polysiloxane, and separating the modified polysiloxane optionally washed and then dried.

* * * * *